(12) United States Patent
Shi et al.

(10) Patent No.: US 11,807,847 B2
(45) Date of Patent: Nov. 7, 2023

(54) STRAIN OF ENTEROBACTER FOR DEGRADING HYALURONIC ACID AND APPLICATION THEREOF

(71) Applicants: JIANGNAN UNIVERSITY, Jiangsu (CN); Shandong Focusfreda Biotech Co., Ltd, Shandong (CN)

(72) Inventors: Jinsong Shi, Jiangsu (CN); Zhenghong Xu, Jiangsu (CN); Jinsong Gong, Jiangsu (CN); Wei Liu, Jiangsu (CN); Hui Li, Jiangsu (CN); Jianying Qian, Jiangsu (CN); Lei Liu, Shandong (CN); Qing Li, Shandong (CN); Mengyi Zhang, Shandong (CN); Chuanli Kang, Shandong (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 17/818,240

(22) Filed: Aug. 8, 2022

(65) Prior Publication Data
US 2023/0024365 A1    Jan. 26, 2023

Related U.S. Application Data

(62) Division of application No. 17/134,296, filed on Dec. 26, 2020, now abandoned.

(30) Foreign Application Priority Data

Dec. 26, 2019 (CN) .......................... 201911365498.0

(51) Int. Cl.
    *C12N 1/20*      (2006.01)
    *C12R 1/01*      (2006.01)

(52) U.S. Cl.
    CPC ............... *C12N 1/20* (2013.01); *C12N 1/205* (2021.05); *C12R 2001/01* (2021.05); *C12Y 302/01036* (2013.01)

(58) Field of Classification Search
CPC ...... C12N 1/20; C12N 1/205; C12R 2001/01; C12Y 302/01036
See application file for complete search history.

(56) References Cited

U.S. PATENT DOCUMENTS 10,017,802 B2    7/2018    Corsa et al.

FOREIGN PATENT DOCUMENTS

| CN | 104293726 A | 4/2015 |
| CN | 106497881 A | 3/2017 |

OTHER PUBLICATIONS

Tran Thi Thanh Van,Truong Hai Bang,Tran Nguyen Ha Vy,Quach Thi Minh Thu,Nguyen Thi Nu,Bui Minh Ly,Yuguchi Yoshiaki,Thanh Thi Thu Thuy. Structure, conformation in aqueous solution and antimicrobial activity of ulvan extracted from green seaweed *Ulva reticulata*.[J]. Natural product research,2017.

Darshita Budhadev,Balaram Mukhopadhyay. Chemical synthesis of the pentasaccharide related to the repeating unit of the O-antigen of Enterobacter cloacae G2277[J]. Tetrahedron,2015,71(36).

*Primary Examiner* — Louise W Humphrey
*Assistant Examiner* — Deepa Mishra
(74) *Attorney, Agent, or Firm* — Magstone Law, LLP; Enshan Hong

(57) ABSTRACT

The invention belongs to the field of cosmetic biotechnology, and specifically relates to an *Enterobacter* that degrades hyaluronic acid and a cultivation method and application thereof. The *Enterobacter* sp. CGJ001 of the present invention was deposited in the China General Microbiological Culture Collection Center on Oct. 10, 2019, and the preservation number is CGMCC NO. 18661. The *Enterobacter* strain can efficiently produce hyaluronidase, and can be used in the process of preparing low molecular hyaluronic acid and oligomeric hyaluronic acid from high molecular hyaluronic acid. The enzyme has high specificity towards hyaluronic acid, excellent thermal stability and pH stability, and is suitable for large-scale industrial application. Thus, it can replace the traditional hyaluronidase extracted from expensive animal tissues. There should be broad application prospects in the fields of medicine and cosmetics.

3 Claims, 4 Drawing Sheets

Specification includes a Sequence Listing.

SEQUENCE LISTING

```
Sequence total quantity: 3
SEQ ID NO: 1            moltype =    length =
SEQUENCE: 1
000
```

```
SEQ ID NO: 2           moltype = DNA  length = 18
FEATURE                Location/Qualifiers
misc_feature           1..18
                       note = Synthetic primer 27f
source                 1..18
                       mol_type = other DNA
                       organism = synthetic construct
SEQUENCE: 2
agtttgatcc tggctcag                                              18

SEQ ID NO: 3           moltype = DNA  length = 19
FEATURE                Location/Qualifiers
misc_feature           1..19
                       note = Synthetic primer 1492r
source                 1..19
                       mol_type = other DNA
                       organism = synthetic construct
SEQUENCE: 3
gcttaccttg ttacgactt                                             19
```

STRAIN OF ENTEROBACTER FOR DEGRADING HYALURONIC ACID AND APPLICATION THEREOF

RELATED APPLICATIONS

This application is a divisional application of U.S. application Ser. No. 17/134,296 filed Dec. 26, 2020, which claims the priority from China Patent Application Serial Number CN 201911365498.0, filed on Dec. 26, 2019, the content of which is incorporated here by reference.

REFERENCE TO SEQUENCE LISTING SUBMITTED VIA EFS-WEB

This application includes an electronically submitted sequence listing in .xml format. The .xml file contains a sequence listing entitled "ENTEROBACTER AND ITS APPLICATION.xml" created on Oct. 11, 2022 and is 3,831 bytes in size. The sequence listing contained in this .xml file is part of the specification and is hereby incorporated by reference herein in its entirety.

BACKGROUND OF THE INVENTION

1. Technical Field

The present invention relates to a strain of *Enterobacter* degrading hyaluronic acid and its culture method and application, which belongs to the field of cosmetic biotechnology.

2. Background Art

Hyaluronic acid (HA) is an acidic mucopolysaccharide. Hyaluronic acid is the main component of mammalian extracellular matrix, which is widely present in the intercellular substance of animal tissues and the capsule of some bacteria. Hyaluronic acid (HA) is a straight-chain polysaccharide composed of repeated -D-glucuronic acid and N-acetyl-D-glucosamine disaccharide units, linked by alternating −1,3 glycosidic bonds and −1,4 glycosidic bonds. The molecular weight of hyaluronic acid from different sources is very different and the molecular weight range is very wide.

Hyaluronic acid plays a prominent role in many important physiological and pathological processes in mammals. Hyaluronic acid with different molecular weight has different important meanings for its biological function. High molecular weight HA (MW-HA) exists in healthy tissues and acts as a space filler and lubricant with immunosuppressive properties, while low molecular weight HA (MW-HA) plays an opposite role in immune activation as an endogenous danger signal. HA is often used in the pharmaceutical and cosmetic industries, including drug delivery systems, daily cosmetics, etc., and is an important biocompatible material. However, since the immune properties of HA depend on its molecular weight, the molecular weight of HA must be strictly controlled. Especially for the pharmaceutical industry, it is particularly important to strictly control the molecular weight of hyaluronic acid.

Hyaluronidase degrades hyaluronic acid by breaking the −1,4 glycosidic bond or −1,3 glycosidic bond. According to the substrate specificity of hyaluronidase, the catalytic mechanism and the types of degradation products, hyaluronidase was classified into three types. The first type of hyaluronidase (EC 3.2.1.35) is of bovine testis type. It degrades hyaluronic acid by acting on −1, 4-glucoside bonds. The main product is tetrasaccharide, which can also act on chondroitin sulfate and chondroitin sulfate, and the hydrolytic product is corresponding tetrasaccharide. Typical examples include bovine testis hyaluronidase, bee venom hyaluronidase and lysosomal hyaluronidase. The second type of hyaluronidase (EC 3.2.1.36) is hirudo type. It degrades hyaluronic acid by acting on −1, 3-glucoside bonds. Its degradation products contain tetrasaccharides and hexoses and cannot act on chondroitin sulfate and chondroitin sulfate. Typical examples are hirudo hyaluronidase and hookworm salivary gland hyaluronidase. The third type of hyaluronidase (EC 4.2.2.1) is from microbial sources and widely distributed in bacteria, pathogenic fungi and phages. It degrades hyaluronic acid to produce unsaturated disaccharides by acting on −1, 4-glucoside bonds and elimination reactions, and also acts on chondroitin and chondroitin sulfate. Examples include *Clostridium, Micrococcus, Streptococcus* and *Streptomyces*.

Hyaluronidase is widely used in cardiology, ophthalmology, plastic surgery, oncology, dermatology and gynecology, etc. Hyaluronidase can effectively slow down myocardial infarction by reducing myocardial hyaluronic acid content, reducing arterial resistance caused by myocardial ischemia, and increasing blood flow. The combined action of hyaluronidase and anticancer drugs can enhance the efficacy of anticancer drugs and play an important role in enhancing the anti-breast cancer effect of adriamycin and reducing the recurrence rate of bladder cancer. Hyaluronidase can "destroy" the hyaluronic acid around the tumor tissue, and has a certain inhibitory effect on the tumor growth. Using hyaluronidase as a dispersant can hydrolyze mucopolysaccharide, promote the absorption of therapeutic drugs, and accelerate the diffusion and absorption of local accumulation fluid and exudate. In addition, as an anesthetic assistant, hyaluronidase can effectively promote the dispersion and absorption of anesthetic drugs, shorten the duration of anesthesia, and increase the depth of anesthesia. However, many problems have been found in the application of hyaluronidase. Therefore, the new hyaluronidase with new properties will become the research hotspot in the future. So far, hyaluronidase has been reported mainly from *Streptococcus*, while the enzymes from *Enterobacter* sp. has never been reported.

SUMMARY OF THE INVENTION

In view of the present hyaluronidase used widely, but the shortage of enzyme resources, the present invention provides a kind of *Enterobacter* CGJ001 (*Enterobacter* sp.), the species preservation in China General Microbiological Culture Collection Center (CGMCC) on Oct. 10, 2019, microbial preservation management committee address: Beijing Chaoyang District Beichen West Road No. 1 Hospital No. 3, the Institute of Microbiology, Chinese Academy of Sciences, preservation number CGMCC NO. 18661.

The above-mentioned *Enterobacter* sp. CGJ001 is gram-negative with short rod-shaped bacteria, as shown in FIG. 1~3.

The *Enterobacter* sp. CGJ001 strain has been molecularly identified and sequenced, and its 16S rRNA gene sequence length is 1381 bp, as shown in SEQ NO. 1. By using the BLAST program of the National Center for Biotechnology Information (NCBI), the results show that the 16S rDNA sequence of this strain is comparable to that of *Enterobacter* (JQ795804.1, KJ184972.1, MH883957.1, etc.) The related sequences have more than 99.8% homology, and they are finally classified as *Enterobacter* strains.

In one embodiment, the *Enterobacter* CGJ001 has the effect of degrading hyaluronic acid.

Another object of the present invention is to provide an application of *Enterobacter* CGJ001 in the production of hyaluronidase.

In one embodiment, hyaluronidase was prepared from the *Enterobacter* CGJ001 through plate culture, seed culture and fermentation culture.

In one embodiment, the application specifically includes the following steps:
(1) Plate culture of *Enterobacter* CGJ001 to obtain plate strains;
(2) Inoculate the plate strains into the sterilized seed culture medium and incubate at 30-40° C. and 150-300 rpm for 12-24 h to obtain seed liquid;
(3) Inoculate the seed liquid into a sterilized fermentation medium and incubate at 30-40° C. and 150-300 rpm for 12-24 h to obtain a hyaluronidase-containing bacterial liquid.

In one embodiment, the seed medium and fermentation medium components include 1~10 g/L hyaluronic acid, 1~5 g/L $K_3PO_4$, 0.1~1 g/L $MgSO_4$, 1~10 g/L peptone, 1~10 g/L yeast powder.

In one embodiment, the pH value of the seed medium and the fermentation medium is 6-8.

In one embodiment, the composition per liter of the plate culture medium is as follows:

Peptone 1~10 g, yeast powder 1~10 g, sodium hyaluronate 1~10 g, $K_3PO_4 \cdot 3H_2O$ 1~5 g, $MgSO_4 \cdot 7H_2O$ 0.1~1 g, water 1000 mL, agar powder 15~25 g, The pH value is 6-8.

The above-mentioned *Enterobacter* CGJ001 bacterial liquid prepares the crude hyaluronidase liquid, the steps are as follows:
(i) Centrifuge the bacterial liquid of *Enterobacter* CGJ001 obtained in step (3) to obtain the bacterial cells, and the conditions of the centrifugation are: 6000 rpm for 10-15 min;
(ii) Discard the supernatant of the above centrifugal liquid, add an equal volume of PBS solution to resuspend the bacteria;
(iii) The above-mentioned resuspended bacterial cells were subjected to ultrasonic cell disruption for 20 minutes to prepare a crude hyaluronidase solution.

The components per liter of the ABOVE PBS solution are as follows:
2-3 g of sodium dihydrogen phosphate, 0.5-2 g of anhydrous disodium hydrogen phosphate and 5-10 g of sodium chloride, 1000 mL of water, pH5~7.

Hydrochloric acid and sodium hydroxide were used to adjust the pH of the above PBS Solution The parameters of the ultrasonic crushing instrument were set as follows: ultrasonic time 20 min, breaking for 4 S and stopping for 6 S, power 300 W.

In one embodiment, the hyaluronidase prepared by any of the above-mentioned hyaluronidase preparation methods is analyzed by mass spectrometry, and the degradation product of hyaluronidase by the enzyme is 2-6 sugars.

The invention has the advantages of:

The *Enterobacter* CGJ001 of the present invention has excellent enzyme activity, strong specificity for hyaluronic acid, good thermal stability and pH stability, and is suitable for scale-up production, thereby replacing hyaluronidase extracted from expensive animal tissues. It has a broad application prospect in the fields of medicine and cosmetics.

DESCRIPTION OF PREFERRED EMBODIMENTS

Figure 1:
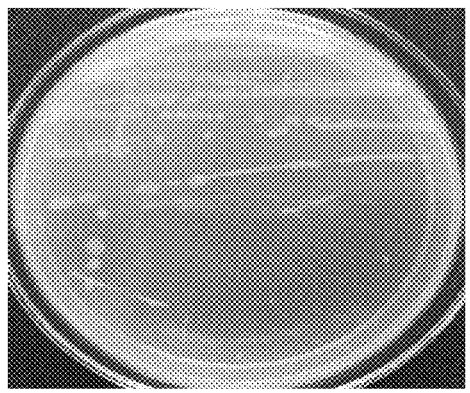
FIG. 1 shows the colony morphology of *Enterobacter* CGJ001 strain on solid medium.
Figure 2:
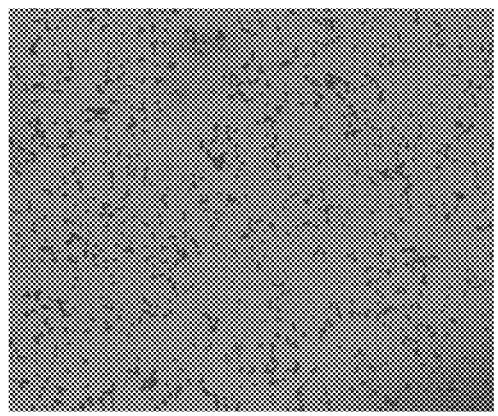
FIG. 2 shows the optical microscope photos of *Enterobacter* CGJ001 strain.
Figure 3:
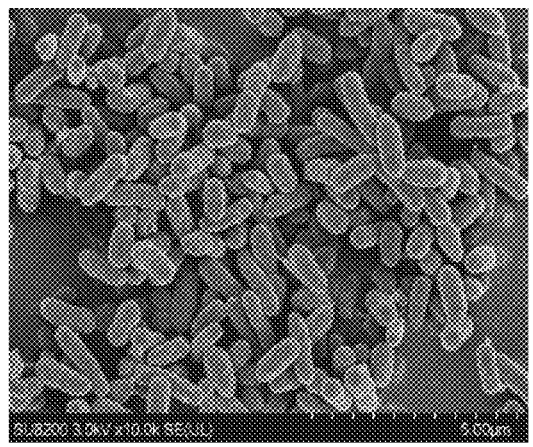
FIG. 3 shows the electron microscope images of *Enterobacter* CGJ001 strain.

The detailed implementation of the invention is further described as follows. The following embodiments are used to illustrate the invention, but not to limit the scope of the invention.

Technicians in this field can clearly understand the characteristics and efficacy of the invention from the contents explained in this specification, and the invention can also be implemented or applied in other specific ways.

Example 1

A polluted river water sample from Wuxi, Jiangsu province was taken and 1 mL supernatant was added to 9 mL normal saline, which was diluted to 5 concentration gradients of $10^{-4}$, $10^{-5}$, $10^{-6}$, $10^{-7}$, $10^{-8}$, respectively. The diluted bacterial suspension was coated on the screening medium.

Two parallel cultures under each concentration were carried out at a concentration of 30° C. for 5 days. The single colonies with good growth were picked out, then seeded in liquid culture and coated in solid medium. Then the single colony was selected in liquid culture medium for cultivation at 30° C. and 220 rpm for 24 h. 0.9 mL of the culture substance was added to 0.9 mL 40% glycerol, which was mixed and stored in the refrigerator at −80° C. for a long time.

The components of the above screening medium per liter are as follows:

Sodium hyaluronate (5 g), $K_3PO_4 \cdot 3H_2O$ (2 g), $MgSO_4 \cdot 7H_2O$ (0.5 g), water (1000 mL), and agar (20 g) were added as the screening medium.

The components per liter of the seed medium are as follows:

Peptone 5 g, yeast 5 g, sodium hyaluronate 5 g, $K_3PO_4 \cdot 3H_2O$ 2 g, $MgSO_4 \cdot 7H_2O$ 0.5 g, water 1000 mL, pH 6.

The components of the solid medium per liter are as follows:

Peptone 5 g, yeast 5 g, sodium hyaluronate 5 g, $K_3PO_4 \cdot 3H_2O$ 2 g, $MgSO_4 \cdot 7H_2O$ 0.5 g, water 1000 mL, pH 6, and agar 20 g were added.

The application of *Enterobacter* CGJ001 in the production of hyaluronidase is as follows:

(1) Take *Enterobacter* CGJ001 for plate culture to obtain plate strains;
(2) Inoculate the plate strains into the sterilized seed culture medium, and incubate at 30° C. and 150 rpm for 12 hours to obtain seed liquid;
(3) Inoculate the seed liquid into a sterilized fermentation medium, and cultivate for 12 hours at 30° C. and 150 rpm to obtain a hyaluronidase-containing bacterial liquid.

The seed medium and fermentation medium components include 1 g/L hyaluronic acid, 1 g/L $K_3PO_4$, 0.1 g/L MgSO4, 1 g/L peptone, and 1 g/L yeast powder. The pH value of the seed medium and the fermentation medium is 6.

The components per liter of the flat culture medium are as follows:

Peptone 5 g, yeast 5 g, sodium hyaluronate 5 g, $K_3PO_4·3H_2O$ 2 g, $MgSO_4·7H_2O$ 0.5 g, water 1000 mL, agar 20 g, pH 6.

The above-mentioned bacterial solution of *Enterobacter* CGJ001 was used to prepare crude hyaluronidase solution. The steps are as follows:
(i) Take step (3) The hyaluronidase containing bacteria solution prepared by centrifugation to obtain the bacteria body, the centrifugation conditions are as follows: 6000 rpm for 10 min;
(ii) Discard the supernatant of the centrifugal liquid and add the bacteria to PBS solution for resuspended suspension at the same volume;
(iii) The resuspended bacteria were broken by ultrasonic disruption for 20 min to prepare the crude hyaluronidase solution.

The components per liter of the above PBS solution are as follows:
2.5 g sodium dihydrogen phosphate, 1.0 g disodium hydrogen phosphate and 8.2 g sodium chloride anhydrous, 1000 mL water, pH 6.2.
Hydrochloric acid and sodium hydroxide are used to adjust the pH of the above PBS Solution The parameters of the ultrasonic disruption instrument are set as follows: ultrasonic time 20 min, breaking 4 S and stopping 6 S, power 300 W.

Example 2

The specific method for measuring the enzyme activity of crude hyaluronidase solution is as follows:
Preparation of DNS Solution:
Weigh (10±0.1) g of 3,5-dinitrosalicylic acid, place it in about 600 mL of water, gradually add 10 g of sodium hydroxide, stir to dissolve in a 50° C. water bath (magnetic force), and then add 200 g of potassium tartrate Sodium, phenol 2 g, and anhydrous sodium sulfite 5 g sequentially. After all above were dissolved and clarified, cool it to room temperature, dilute to 1000 mL with water, and filter. Store it in a brown reagent bottle, and place it in a dark place for 7 days. (Preparation of standard DNS reagent according to the standard procedure of Ministry of Light Industry)

The total reaction system was 3 mL. Add 0, 50, 100, 150, 200 μL glucose standard solution (2 mg/mL) to 2 mL DNS solution respectively, add water to make up to 3 mL, boil it in a boiling water bath for 10 minutes, and then cool it to room temperature, and add water to make up to 10 mL. The absorbance was measured at 540 nm, the absorbance was taken as the abscissa, and the glucose concentration was taken as the ordinate to make a standard curve.

The determination steps of the crude hyaluronidase solution sample are as follows:
The following reagents are required: 2 mg/mL hyaluronic acid, 50 mmol/L, pH 6.0 PBS buffer. The reaction system was 1 mL, including 800 μL hyaluronic acid, 100 μL of crude hyaluronidase solution, adding PBS buffer to make up 1 mL, reacting in a 39° C. water bath for 15 min. The absorbance value was measured and substituted into the standard curve to obtain the reduced equivalent glucose mass concentration, replacing the glucose standard solution with 1 mL of the reaction sample.

A unit of enzyme activity is defined as: under the above experimental conditions, the amount of enzyme required to produce 1 μg of glucose per 1 h is defined as a unit of enzyme activity.

The *Enterobacter* CGJ001 of the present invention has a fermentation enzyme activity of 8139 U/mL.

Example 3

As shown in FIG. 1, the solid medium plate, optical microscope and electron microscope morphology of *Enterobacter* CGJ001 were observed and identified. The results showed that the colony of the strain on the hyaluronic acid solid medium plate was a convex colony, the surface was smooth, moist, crystal clear, and the color was milky white, which was easy to pick. When observed under a light microscope, the cells are short rod-shaped. This strain is a short gram-negative rod-shaped bacterium, without capsule, spores and flagella, and can grow with hyaluronic acid as the only carbon source.

The above general primers for gene amplification of bacterial strains are:

```
The forward primer is 27f:
                            (SEQ ID NO: 2)
5'-AGTTTGATCCTG GCT CAG-3';

The reverse primer is 1492r:
                            (SEQ ID NO: 3)
5'-GCTTACCTTGTTACGACTT-3'
```

The above reaction system for strain gene amplification is as follows, the total volume is 20 μL:

| | |
|---|---|
| Forward primer 27f with a concentration of 10 mmol/L | 1 μL |
| Reverse primer 1492r with a concentration of 10 mmol/L | 1 μL |
| 2xES-taq enzyme | 10 μL |
| Ultra-pure water | 8 μL |

And pick a single colony on the solid medium and mix it in the system.

gene amplification reagents used were purchased from Sangon Biotech (Shanghai) Co., Ltd.

The above procedures for strain gene amplification were pre-denaturation at 95° C. for 10 min, denaturation at 95° C. for 30 S, annealing at 55° C. for 30 S, extension at 72° C. for 90 S, a total of 34 cycles, extension at 72° C. for 15 min, and insulation at 4° C.

The 16S rDNA sequence length of this strain is 1381 bp. Blast comparison of the sequence in NCBI database shows that 16S rDNA sequence of this strain is over 99.8% homologous with relevant sequences of *Enterobacter* (JQ795804.1, KJ184972.1, MH883957.1, etc.), and finally it is classified as *Enterobacter* strains. *Enterobacter* sp.

CGJ001 was identified by combining its morphological and physiological and biochemical characteristics. This strain has been stored in the China General Microbiological Culture Collection Center, with the storage address being No. 3, Yard No. 1, Beichen West Road, Chaoyang District, Beijing, and the preservation number is CGMCC No. 18661.

Example 4

The crude hyaluronidase enzyme solution prepared by Example 1 was added to 50 mL 10 g/mL sodium hyaluronate solution according to 5% enzyme dosage, and was put into a thermostatic water bath at 39° C. for reaction. The initial viscosity of the system was 1405 cP. The viscosity of the system was measured every 10 min, 1 mL was sampled, and the absorbance was inactivated by boiling for 2 min. Then, DNS method was used to measure the absorbance at different time periods.

Figure 4:
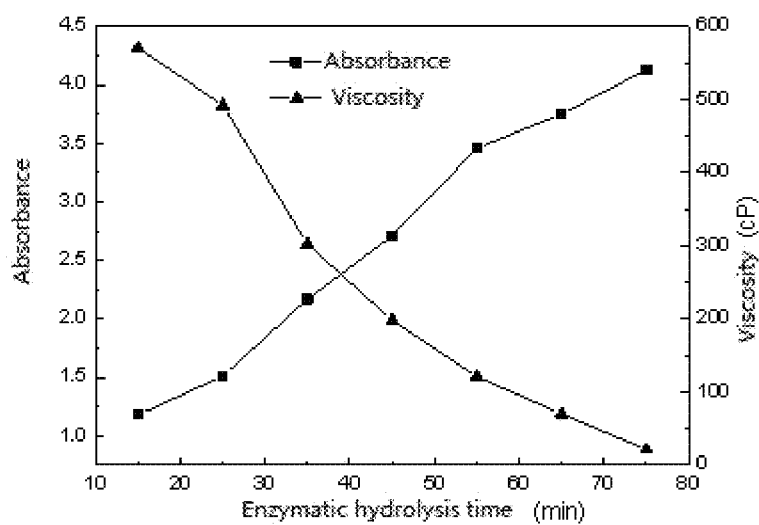
FIG. 4 shows the effect of degradation of crude hyaluronidase enzyme solution on the viscosity of sodium hyaluronate.

As shown in FIG. 4, with the increase of enzymatic hydrolysis time, the viscosity of sodium hyaluronate solution decreases, and the absorbance of DNS reaction of the whole system increases. This result indicates that as the time of enzymatic hydrolysis increases, the viscosity of sodium hyaluronate decreases, and the number of oligosaccharides with reducing ends produced increases.

Using the crude enzyme preparation from *Enterobacter* CGJ001 to analyze the degradation ability of different polysaccharides:

After mixing the polysaccharide substrate with a concentration of 2 mg/mL, PBS buffer and the crude hyaluronidase enzyme solution prepared in Example 1 in a ratio of 8:1:1 (volume ratio), the mixed solution was reacted at 39° C. for 4 hours, incubated in a boiling water bath for 5 minutes to inactivate the enzyme, and centrifuged at 8000 rpm at 4° C. for 10 minutes. Then the supernatant was taken as the enzymolysis product of the crude enzyme liquid preparation prepared by *Enterobacter* CGJ001. The reducing sugar produced was detected by the DNS method.

The results are shown in Table 1. The crude hyaluronidase enzyme solution prepared by *Enterobacter* CGJ001 has high specificity for hyaluronic acid, and no degradation ability for sodium alginate and chitosan, so it has potential application value.

TABLE 1

Degradation ability on different polysaccharides of crude enzyme solution prepared by Enterobacter CGJ001

| Types of polysaccharides | Sodium hyaluronate | Chitooligo-saccharides | Sodium Alginate |
|---|---|---|---|
| Ability of degradation | + | − | − |

Note:
"+" means biodegradable,
"−" means non-biodegradable.

Figure 7:
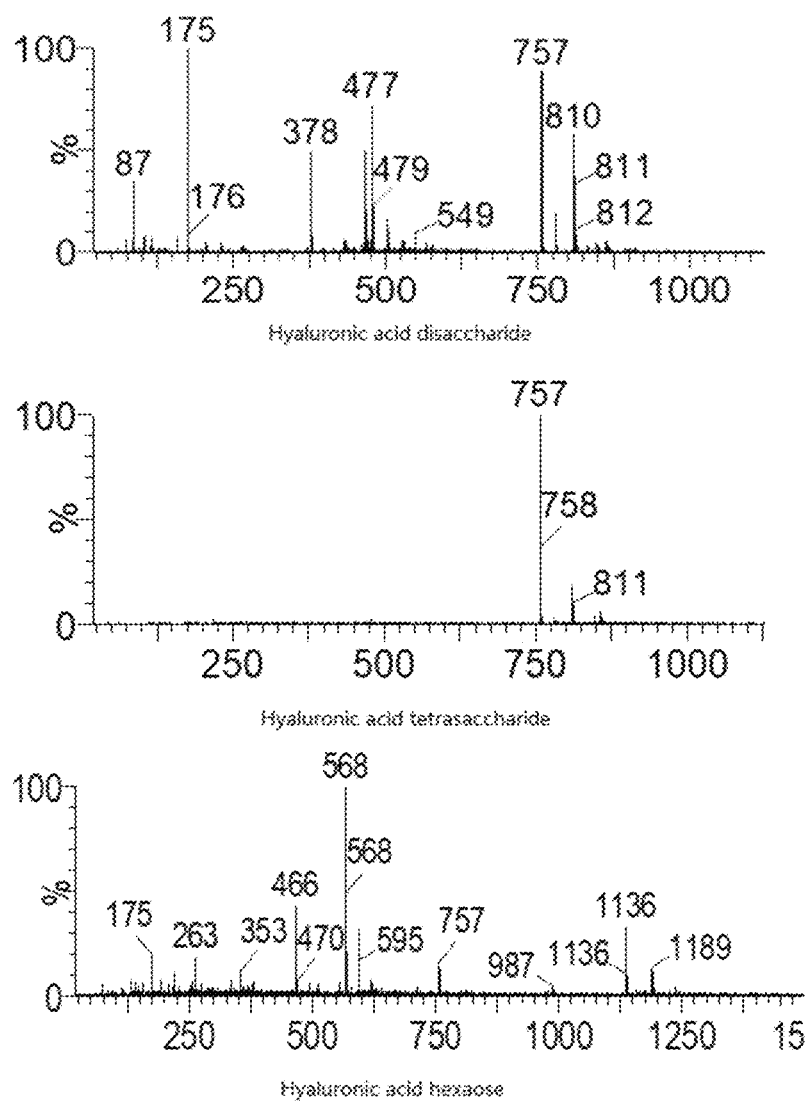
FIG. 7 shows the mass spectrometric analysis of unsaturated oligosaccharides prepared by crude enzyme solution in example 5.

The results of mass spectrometry in anion mode showed that the oligosaccharide products obtained by degrading hyaluronic acid with the crude hyaluronic acid solution prepared in Example 1 were: hyaluronic acid disaccharide with a molecular weight of 379, the transparent hyaluronic acid with a molecular weight of 758, and the tetrasaccharide of tetrasaccharide, hyaluronic hexasaccharide with a molecular weight of 1137, as shown in FIG. 7.

Example 5

After mixing hyaluronic acid with a concentration of 2 mg/mL, PBS buffer and the crude hyaluronidase enzyme solution prepared in Example 1 at a ratio of 8:1:1 (volume ratio), three parallel experiments were performed. Put them in a water bath at 35° C., 37° C., 39° C., 41° C., and 43° C. separately for 1 hour, and then remove them into another water bath at 100° C. for 5 minutes to inactivate. Then add 2 ml DNS reagent separately and put them in a 100° C. water bath to react for 10 minutes, then take them out and cool to room temperature. Measure their absorbance with UV spectrophotometer at 540 nm.

Relative enzyme activity is defined as: the percentage of the average absorption value of each group and the maximum absorption value. The maximum absorption value corresponds to the optimal reaction temperature of the crude enzyme solution.

Figure 5:
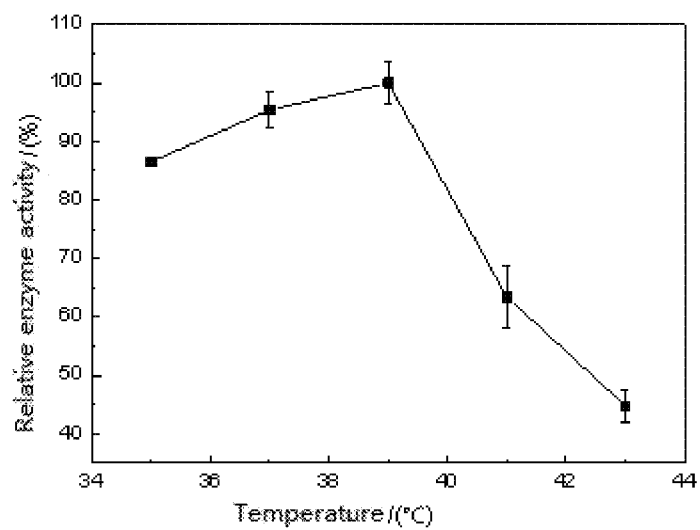
FIG. 5 shows the optimal reaction temperature of the crude hyaluronidase solution.

The results of the optimal reaction temperature of the crude hyaluronidase enzyme solution are shown in FIG. 5, and the optimal reaction temperature of the crude hyaluronidase enzyme solution is 39° C.

Research on the Optimum Reaction pH of Crude Hyaluronidase Enzyme Solution

Prepare hyaluronic acid solutions with a concentration of 2 mg/mL using phosphate buffers with pH 4, 5, 6, 7, and 8, respectively. After the hyaluronic acid is completely dissolved, it is incubated at the optimum temperature of 39° C., and then 100 μL of the crude hyaluronic acid solution prepared in Example 1 is added to every 900 μL of the hyaluronic acid solution of different pH. After mixing them uniformly, they were placed in a 39° C. water bath to react for 1 h, and 3 parallel samples were set up under each condition.

Relative enzyme activity is defined as: the percentage of the average absorption value of each group and the maximum absorption value. The maximum absorption value corresponds to the optimum pH of the crude enzyme solution.

Figure 6:
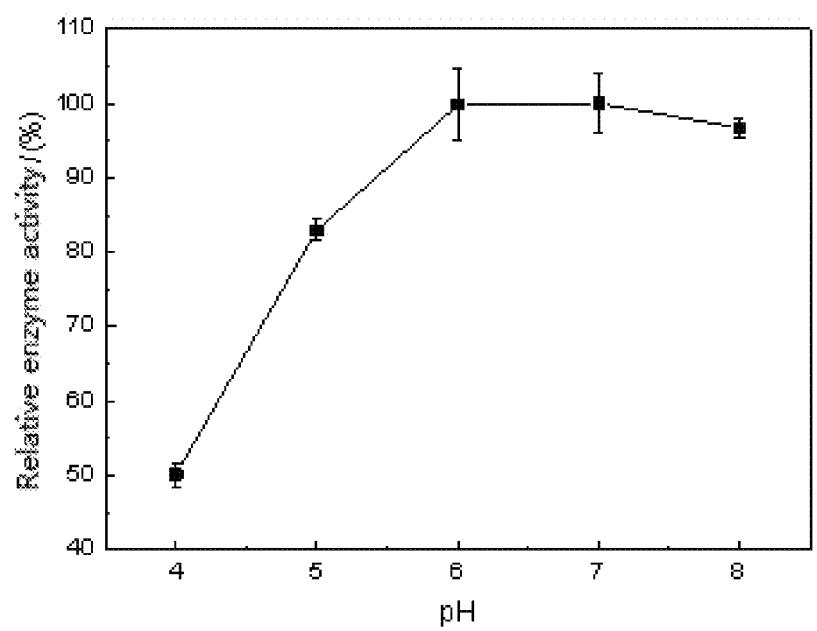
FIG. 6 shows the optimal pH of the crude hyaluronidase enzyme solution in Example 5.

The results of the optimal reaction pH of the crude hyaluronidase solution are shown in FIG. 6, and the optimal reaction pH of the crude hyaluronidase solution is 6-7.

The above-mentioned examples are only preferred examples for fully explaining the present invention, and the protection scope of the present invention is not limited thereto. The equivalent substitution or transformation made by technicians in the technical field on the basis of the present invention shall be within the protection scope of the present invention. The scope of protection of the invention shall be governed by the claim.

We claim:

1. A method of producing hyaluronidase comprising subjecting an isolated strain of *Enterobacter* CGJ001 deposited at China General Microbiological Culture Collection Center with Accession Number CGMCC NO. 18661 to plate culture, seed culture, and fermentation culture.

2. The method of claim 1 comprising:
   (1) plate culturing the isolated strain of *Enterobacter* CGJ001 to obtain plate strains;
   (2) inoculating the plate strains into sterilized seed culture medium and incubating at 30-40° C. and 150-300 rpm for 12-24 h to obtain seed liquid; and
   (3) inoculating the seed liquid into a sterilized fermentation medium and incubating at 30-40° C. and 150-300 rpm for 12-24 h to obtain a hyaluronidase-containing bacterial liquid.

3. The method of claim 2 wherein each of the seed culture medium and fermentation medium independently comprises 1 ~10 g/L hyaluronic acid, 1 ~5 g/L K3PO4, 0.1 ~1 g/L MgSO4, 1 ~10 g/L L peptone, 1 ~10 g/L yeast powder.

* * * * *